United States Patent
Sibbons et al.

(10) Patent No.: US 10,226,547 B2
(45) Date of Patent: Mar. 12, 2019

(54) IMPLANT AND METHOD FOR PRODUCING AN IMPLANT

(71) Applicant: Videregen Limited, Liverpool (GB)

(72) Inventors: Paul David Sibbons, Harrow (GB); Tahera Iqbal Ansari, Harrow (GB)

(73) Assignee: VIDEGREN LIMITED (GB)

( * ) Notice: Subject to any disclaimer, the term of this patent is extended or adjusted under 35 U.S.C. 154(b) by 140 days.

(21) Appl. No.: 14/415,016

(22) PCT Filed: Jul. 16, 2013

(86) PCT No.: PCT/GB2013/051898
§ 371 (c)(1),
(2) Date: Jan. 15, 2015

(87) PCT Pub. No.: WO2014/013241
PCT Pub. Date: Jan. 23, 2014

(65) Prior Publication Data
US 2015/0190548 A1   Jul. 9, 2015

(30) Foreign Application Priority Data
Jul. 18, 2012  (GB) .................................. 1212771.8

(51) Int. Cl.
A61F 2/04 (2013.01)
A61L 27/36 (2006.01)

(52) U.S. Cl.
CPC ............ *A61L 27/3629* (2013.01); *A61F 2/04* (2013.01); *A61L 27/3691* (2013.01); *A61F 2002/045* (2013.01)

(58) Field of Classification Search
CPC ............ C12N 2533/92; C12N 2533/90; A61L 27/3629; A61L 27/3691; A61F 2/04
See application file for complete search history.

(56) References Cited

U.S. PATENT DOCUMENTS

2004/0234507 A1  11/2004  Stone
2010/0093066 A1   4/2010  Taylor et al.

FOREIGN PATENT DOCUMENTS

WO  9632905 A1  10/1996
WO  2007025233 A1  3/2007

OTHER PUBLICATIONS

Gilbert et al., Decellularization of tissues and organs. Biomaterials, vol. 27, No. 19 (Jul. 2006) pp. 3675-3683.*
International Search Report for PCT/GB2013/051898, dated Apr. 10, 2013, 3 pages.
PCT, Third Party Observation for PCT/GB2013/051898, dated Jul. 23, 2014, 4 pages.
UK Search Report for GB1212771.8, dated Nov. 16, 2012, 4 pages.
Mertsching et al., "Engineering of a Vascularized Scaffold for Artificial Tissue and Organ Generation", Biomaterials, vol. 26, 2005, pp. 6610-6617.
Totonelli et al., "A Rat Decellularized Small Bowel Scaffold that Preserves Villus-Crypt Architecture for Intestinal Regeneration" Biomaterials, vol. 33, 2012, pp. 3401-3410.
Hirsh et al., "Cholecystokinin Decreases Intestinal Hexose Absorption y a Parallel Reduction in SGLT11 Abundance in the Brush-Border Membrane", The Journal of Biological Chemistry, vol. 273, No. 23, Jun. 1998, pp. 14545-14549.
Lautenschlager et al., "A Model of the Isolated Perfused Rat Small Intestine" Am. J. Physiol. Gastrointest Liver Physiol., vol. 298, 2010, pp. G304-G313.
Mertsching et al. "Generation and Transplantation of an Autologous Vascularized Bioartificial Human Tissue" Transplantation, vol. 88, No. 2, 2009, pp. 203-210.
Schanz et al., Vascularised Human Tissue Models: A New Approach for the Refinement of Biomedical Research Journal of Biotechnology, vol. 148, 2010, pp. 56-63.
Linke et al., "Engineered Liver-Like Tissue on a Capillarized Matrix for Applied Research" Tissue Engineering, vol. 13, No. 11, 2007, pp. 2699-2707.
Crapo, et al., "An Overview of Tissue and Whole Organ Decellularization Processes" Biomaterials, vol. 32, 2011, pp. 3233-3243.
Eberli et al., "Tissue Engineering Using Adult Stem Cells" Methods in Enzymology, vol. 420, 2006, pp. 287-302.

* cited by examiner

*Primary Examiner* — Kara D Johnson
(74) *Attorney, Agent, or Firm* — Tarolli, Sundheim, Covell & Tummino LLP

(57) ABSTRACT

The invention relates to an implant derived from intestinal tissue and to an improved method for producing an implant from intestinal tissue. According to the invention, intestinal tissue comprising a tubular segment of intestine with at least part of its associated vasculature intact is processed by: perfusing the vasculature through a vessel thereof with at least one decellularizing medium; and separately perfusing the tubular segment of intestine through its lumen with at least one decellularizing medium. The new method greatly improves tissue processing as compared with the methods previously known in the art, in which decellularization solutions were perfused into the tissue via the vasculature only, relying on diffusion to decellularize and purify the small bowel tissue. In contrast, the invention provides for separate decellularization and purification protocols for the vascular and tubular intestinal components, which are designed to optimize decellularization and purification of each of these tissue structures while preserving certain tissue-specific three-dimensional structures. The resulting scaffold is substantially decellularized and provides an excellent implant for repair and regeneration of bowel tissue.

8 Claims, 7 Drawing Sheets

IMPLANT AND METHOD FOR PRODUCING AN IMPLANT

TECHNICAL FIELD

The present invention relates to a implant and to a method for producing an implant. The invention is particularly useful in the production of implants derived from intestine.

BACKGROUND

Implants comprising biologically derived scaffolds have become important options for tissue/organ repair and regeneration in the treatment of various different diseases and conditions. A continuing major hurdle is the need for a functional blood supply for the implanted scaffold.

Patients short bowel syndrome (SBS) lack more than half of their small intestine, which may be caused by a number of disorders and typically results in surgical resection. Suitable implants would be useful in the treatment of SBS. Bowel diseases, such as Crohn's disease in adults and necrotising enterocolitis in infants, are diseases which can lead to short bowel syndrome (SBS) and consequent nutrient absorptive failure requiring a bowel transplant. This is a significant clinical issue resulting in poor quality of life, shortened life expectancy and reliance on expensive chronic care regimes for survival. It is estimated that £700 million per annum is spent on parenteral nutrition alone (excluding nursing and other care) for SBS in the EU and US.

Previous studies have used both synthetic and biological scaffolds to produce short segments of neo-intestinal tissue. For example, de-cellularised porcine small intestine submucosa (SIS), a collagen based acellular matrix used for the regeneration or augmentation of diseased or non-functional biological systems, has been successfully employed to regenerate neo-intestine in small animal models. However, SIS does not retain the original vascular supply to the tissue, resulting in limited perfusion. Additionally, SIS has relatively poor mechanical and regenerative properties.

A critical hurdle in the ability to create thick complex or multilayered tissue is the requirement of a suitable vascular supply which can be the limiting factor governing the size of tissue construct. With this in place, the translation of small-scale scaffold implantation to larger grafts of real clinical relevance becomes more feasible. A pre-existing or rapidly developing vascular supply to an implanted scaffold has to be able to provide all the necessary oxygen, nutrients and growth factor(s) to ensure survival. Diffusion distances of 100 µm-200 µm limit the survival of cells from the nearest capillary and since blood vessels can take days to develop, the lack of available oxygen can potentially predispose the implant to ischemia.

Vascularisation methods have tended to focus on the synthesis of de-novo blood vessels rather than the utilization of existing vasculature attached to the biological scaffold. Since the growth of host vessels into an implanted graft can take a few weeks to occur, the grafts are often threatened by ischemia and necrosis.

Recently, a group in Germany has developed a method to obtain a biological scaffold with a feeding artery and vein as an integral part of the scaffold. The vasculature can be directly anastomosed to the host's blood supply and presents the possibility of either re-endothelisation when attached to the host or in vitro prior to implantation (Linke et al. (2007) *Tissue Engineering* 13(11); 2699-2707: Mertsching et al. (2009) *Transplantation* 88(2): 203-210; Schanz et al. (2010) *Journal of Biotechnology* 148(1): 56-63).

SUMMARY

The present invention provides an improved method for producing an implant for tissue/organ repair, the implant being derived from intestinal tissue.

According to a first aspect of the present invention there is provided a method for producing an implant from intestinal tissue, the intestinal tissue comprising a tubular segment of intestine with at least part of its associated vasculature intact, the method comprising:

perfusing the vasculature through a vessel thereof with at least one decellularising medium, and separately perfusing the tubular segment of intestine through its lumen with at least one decellularising medium.

The resulting scaffold provides an excellent implant for repair and regeneration of bowel tissue. The scaffold comprises a patent feeding artery, a draining vein and microvascular connections. The method of the present invention can be applied to short segments of intestine to provide implants that allow a reduction in parenteral nutrition requirements in SBS and intestinal failure patients, or to segments that are long enough to provide implants that allow complete cessation of parenteral nutrition requirements.

The scaffold incorporates two components: the tubular component derived from the tubular segment of intestine and the vascular component derived from the associated vasculature. When implanted, the vascular compontent of the scaffold provides an immediate route for the delivery of blood into the scaffold and feeds oxygen and nutrients to the scaffold as it regenerates in the implant recipient. The vascular component delivers systemic blood deep into the villi of the tubular component of the scaffold.

The vasculature is preferably perfused by introducing the decellularising medium through an artery thereof, most preferably the main artery or one of the main arteries. The artery may be cannulated to facilitate perfusion. The decellularising medium may leave the vasculature via a vein, such as the main vein or one of the main veins.

To facilitate perfusion of the tubular segment of intestine, input and/or output means may be provided. For instance, tubes may be attached to a proximal and/or distal end of the tubular segment of intestine, for example by tying or stitching.

A pump is typically used to ensure effective perfusion.

The method may be used to provide a substantially decellularised scaffold in which cells are substantially removed, the scaffold having had removed sufficient cellular material and associated components such that no adverse tissue reactivity or immune reaction is observed in vivo. Reactivity may be measured by subcutaneous implantation. The substantially decellularised scaffold is free from cells as visualised by microscopy at ×40 magnification.

In a recent review of tissue and whole organ decellularisation processes (Crapo et al. (2011) *Biomaterials* 32: 3233-3243) it was proposed that the following minimal criteria, in addition to the lack of adverse in-vivo response, suffice to satisfy the intent of extracellular matrix (ECM) decellularisation: <50 ng dsDNA per mg ECM dry weight; <200 bp DNA fragment length; and lack of visible nuclear material in tissue sections stained with DAPI or H&E.

These criteria are satisfied by the present invention, the remaining DNA in representative ileum-derived scaffolds according to the present invention having been found to be typically less than 1% of native tissue (both ileum and blood vessels). This is comparable to the amounts of DNA found in commercially available acellular biological matrices used in clinical applications, and significantly less than the nuclear content found in other ECM scaffolds under pre-clinical investigation. In particular, Mertsching et al. reported residual DNA measurements 100 times greater than those typically obtained by the present invention. Higher residual DNA content may lead to sub-optimal cellular and tissue responses due to host reaction to the residual DNA, which will affect the regenerative capabilitiy of the tissue.

The remaining scaffold comprises ECM, in particular collagen and elastin. The collagen typically comprises mainly Type I collagen plus Type II and Type V collagen. For example, collagen analysis of a representative scaffold according to the present invention revealed around 68% Type I collagen, around 20% Type III collagen and around 12% Type V collagen.

The collagen and elastin content of natural vascular tissues, and the relative amounts of these proteins, vary considerably between different blood vessels. By way of example, collagen content in some arteries may vary between around 5% and around 25% and in some veins may vary between around 20% and around 45%. Elastin content in some arteries may vary between around 20% and around 60% and in some veins may vary between around 15% and around 40%. It will be appreciated, therefore, that the relative amounts of collagen, elastin and other ECM components may vary according to the starting materials.

Also, it will be appreciated that the relative amounts of the various ECM components typically differ between the tubular component of the scaffold and the vascular component of the scaffold. In the tubular, intestine-derived, component, collagen is typically the predominant protein.

Thus, the decellularised scaffold is non-immunogenic, biocompatible and provides immediate functionality.

Preferably, the structure of the ECM is at least partially preserved in the scaffold and is preferably substantially preserved. Thus, the scaffold may comprise collagen fibres and/or elastin fibres displaying original fibre architecture and molecular ultrastructure of the natural tissue material from which it is derived. The natural three-dimensional structures of these fibrous tissue proteins are preferably substantially retained.

It is known that cellular components specific for the scaffold's origin and/or the place of its implantation will invoke proper constructive remodelling of the ECM only when the unique polymeric architecture of the fibres within the decellularised tissues or organs remains a least partially intact. Therefore, ECM is better suited than any synthetic matrix to elicit functional regenerative remodelling, and provide a successful scaffold for intestinal growth.

Preservation of functional ECM proteins is also important for maintenance of the biological activity, structural integrity, durability and physico-mechanical properties of the scaffold. Maintenance and preservation of the hierarchy of structure from the molecular structure of proteins and GAGs (i.e. amino acid and carbohydrate/sugar sequences, bonds and interactions) through to the macroscopic ultrastructure of the bowel and associated vascular tissues is important for the preservation of the inherent physico-mechanical properties which in turn are important for correct bowel function (movement, expansion and contraction). In addition, cellular function and response is determined in part by structural or topographical cues or signals inherent in the natural tissue. In other words, the tissue structure plays a role in determining cellular fate and differentiation. Therefore, preservation of the three-dimensional structures during decellularisation and tissue processing greatly improves the ultimate cellular repopulation of the bowel and vascular tissue and regeneration of cellular and tissue-specific function.

It is known that the majority of GAGs are either associated with cells or with the ECM. The present invention preferentially preserves ECM-derived/located GAGs while substantially removing the cell-associated GAGs. Thus, the process of decellularisation results in a reduction of total GAGs by removal of cells and cell constituents, including cell-associated GAGs. The ECM-associated GAGs, on the other hand, are preferably largely preserved. This is important as there is 'cross-talk' between ECM GAGS and different cell types, helping to direct cell trafficking, and cell differentiation. The ECM GAGs also serve as a store or sink for growth factors, which helps to direct tissue regeneration after implantation of the scaffold.

The decellularising media are therefore selected so as to deplete the cells and cellular components from the intestinal tissue whilst minimising damage to the ECM proteins, resulting in a scaffold in which ECM structure and function are preserved as far as possible.

Preferably, decellularisation is carried out by perfusion with a number of decellularising solutions. Suitable decellularising media include detergents, such as sodium dodecyl sulphate (SDS), enzymes, such as proteolytic enzymes, for example trypsin, and nucleases, for example deoxyribonucleases (DNases) such as DNase 1, and combinations thereof.

Perfusion may therefore comprise treatment with of series of different media, and may usefully include washing steps with a suitable washing medium or media, such as phosphate buffered saline (PBS).

Perfusion may be carried out in the presence of antibiotics.

Particularly good results have been observed using serial perfusions of solutions of SDS, trypsin and DNase I, washed in between each step using PBS, to break down cells, cytoplasmic components and DNA.

Importantly, and advantageously, the present invention provides for separate decellularisation of the tubular component and the vascular component of the intestinal tissue. Decellularisation of the more fragile vasculature is typically achieved more quickly than the thicker and more complex tubular component. Preferably, therefore, a different perfusion protocol is adopted for each of these components, in order to optimise decellularisation whilst minimising damage to the ECM and its constituents. This provides for more effective, and more efficient, tissue processing and results in an improved scaffold.

Thus, perfusion of the vasculature may be carried out according to a first perfusion protocol and perfusion of the tubular segment of intestine may be carried out according to a second, different, perfusion protocol. The first and second perfusion protocols may differ in their respective decellularising media and/or treatment conditions, including reaction times, concentrations of reagents, etc.

During perfusion, the tissue is typically treated in an incubation medium. The incubation medium may include at least one decellularising medium, to maximise the efficiency of the decellularising process. The decellularisation medium or media may be the same or similar to the decellularisation medium or media used in the perfusion of the vasculature and/or the tubular intestinal component. In preferred embodiments using a series of decellularising solutions for perfusion of the vasculature and/or the tubular component of the intestinal tissue, the same or similar solutions are used as incubation media. Preferably, the compositions of these incubation media substantially correspond to the compositions of the series of decellularising solutions used to perfuse the vascular component of the intestinal tissue.

The method according to the present invention greatly improves tissue processing as compared with the methods previously known in the art, in which decellularisation solutions are perfused into the tissue via the vasculature only, relying on diffusion to decellularise and purify the small bowel tissue. This results in sub-optimal decellularisation and purification of the two tissue types (i.e. the vascular and small bowel tissues), since the process can only be either optimised for one tissue and sub-optimal for the other, or else be generic and sub-optimal for both. Such prior art methods are described in Mertsching et al., the focus of this report appartenly being the provision of a generic tubular tissue structure for use in non-specific tissue reconstruction, and Linke et al., in which decellularised tissue was used as a 'bioreactor' for liver cells. In contrast, the present invention provides for separate decellularisation and purification protocols for the vascular and tubular intestinal components, which are designed to optimise decellularisation and purification of each of these tissue structures while preserving certain tissue-specific three-dimensional structures.

In preferred embodiments, the mucosal layer of the tubular component, which may include the associated microstructure and functionally important macrostructures such as villi and crypts, is at least partially retained in the scaffold. This is in contrast to prior art methods, in which the mucosal layer is removed from the lumen at the small bowel tissue. For instance, Mertsching et al. removed the mucosal structure, presumably as it was not their intention to use the processed small bowel tissue for small bowel repair, but to serve as a generic tubular structure for reconstruction of other tissues. The mucosal layer is preferably not removed in the present invention and is preferably substantially preserved.

It is also preferred that the submucosal layer of the tubular component is at least partially retained in the scaffold. Further, it is preferred that the serosal layer of the tubular component is at least partially retained in the scaffold. Still further, it is preferred that the circular and/or longitudinal muscular layers of the tubular component are at least partially retained in the scaffold. Thus, these tissue layers are preferably not removed and they may be substantially preserved in the implant.

By retaining these key structural components of the tubular, intestinal, portion of the scaffold, the present invention ensures that the anatomy of the scaffold is as close to the original as possible. This has benefits in regeneration of the tissue after implantation such that the tissue structures will be 'recognised' at a cellular level and repopulated by the appropriate specific cell types, thereby aiding differentiation and ensuring that the body does not need to recreate the structural layers. The intact structural layers, in particular the muscular layers, greatly improves the inherent strength of the scaffold, which improves the durability and strength of the implant after implantation. Advantageously, this also helps by ensuring appropriate physical stresses and biomechanical properties, which in turn will contribute to cell development and differentiation.

It has also been observed that the optimised decellularisation and purification methodology according to the present application may preserve nerve and nerve tract structures within the processed small bowel tissue. This is advantageous in that the preserved nerve structures serve as conduits and scaffolds for nerve regrowth and regeneration and are located in generally the correct anatomical and natural positions as preserved from the natural tissue. Bowel funcfion relies on peristaltic movements of the bowel tissue to propel bowel contents along the digestive tract towards the anus. This is in part performed by cellular-derived perstaltic wave propagation and also by nervous stimulation. Therefore, correct bowel peristaltic function requires a combination of nerve-derived and cell-derived stimuli. Both mechanisms are aided by scaffolds according to embodiments of the present invention, through the preservation of three-dimensional tissue structures leading to tissue-specific cellular regeneration and by preservation of nerve tracts to serve as conduits for new nervous regeneration to occur.

The vascular portion of the implant as herein described may be provided as a substantially intact tubular structure, the diameter of which may vary in accordance with the nature of the starting material. It will also be appreciated that the length of the vascular part of the implant may easily be adjusted by appropriate cutting before or after tissue processing, or at any stage during the processing. Thus, in use, the processed vascular portion of the tissue may be cut to the correct size for the particular procedure or implant site.

Preferably, the tunica adventitia of the vascular tissue is at least partially preserved. Preferably also, the tunica media of the vascular tissue is at least partially preserved. Preferably also, the tunica intima of the vascular tissue is at least partially preserved. These tissue structures may be substantially preserved in the implant.

Furthermore, the elastin layer of the internal elastic lamella may be at least partially preserved and is preferably substantially preserved forming an internal, luminal, surface at the vascular portion of the implant.

According to a further aspect of the present invention there is provided an implant derived from intestinal tissue, comprising a tubular component derived from a tubular segment of the intestinal tissue and a vascular component derived from the associated vasculature, wherein a luminal surface of the vascular component comprises the internal elastic lamella which displays original elastin fibre architecture and molecular ultrastructure of the vasculature from which it is derived.

The starting materials for the present invention may be obtained from any human or non-human mammal. In some embodiments, it is preferred that porcine intestinal tissue materials are processed to provide the implant, although it will be understood that other mammalian sources may alternatively be employed.

Small intestine is the preferred intestinal tissue, for example ileum with its attached mesenteric arcade.

The segment of tubular intestine is carefully harvested to minimise the damage to the intestinal tissue.

According to a further aspect of the present invention there is provided a method for producing an implant from intestinal tissue, comprising:

harvesting a tubular segment of intestine from a human or non-human mammal such that at least part of the associated vasculature is retained intact;

perfusing the vasculature through a vessel thereof with at least one decellularising medium, and separately perfusing the tubular segment of intestine through its lumen with at least one decellularising medium.

It has previously been reported that certain parts of the vascular system may be decellularised, such as arteries and veins. Each requires specific decellularisation methodologies to achieve decellularisation without tissue structure damage. The present invention enables decellularisation of the spectrum of vascular tissue ranging from major supplying arteries, small diameter arteries, arterioles, capillaries (both vascular and venous), venules and veins. In essence, the complete vascular system (or vascular 'tree') associated with the intestinal tissue, both feeding and draining the tubular intestinal tissue and integrated within the tubular intestinal tissue, is decellularised by a single protocol substantially without damage or disruption to any aspect.

Thus, the present invention provides a method by which the complete vascular tree associated with the intestinal tissue can be decellularised effectively, while substantially maintaining the ECM and structure of the major and minor vessels of the vascular tissue. This is evidenced in use by the reperfusion of the vascular portion of the decellularised scaffold without significant leakage or thrombosis.

To achieve physiological and biochemical functionality, it may be desirable to reseed the decellularised intestinal scaffold with cells capable of differentiation and development into bowel-specific cell types. Many cell types and sources may be used to achieve this, ranging from allogeneic cells, including stem cells and mixtures of cells, to autologous cells derived from the patient. The selected cells may be manipulated and expanded to provide appropriately differentiated cells in sufficient numbers to reseed the scaffold and/or may be incubated on, and/or in, the decellularised scaffold to allow repopulation and regeneration of cellular population and function. The process may be carried out in a bioreactor.

In some embodiments, it is preferred that the cells are autologous cells, which minimises any potential for immune reaction or rejection of the reseeded cells once implanted into the patient. Furthermore, it is preferable to use adult mesenchymal stem cells derived from adipose tissue (fat) from the patient to recellularise the scaffold. Adipose tissue is the donor tissue of choice as it contains a high proportion of stem cells (Eberli and Atala (2006) *Methods in Enzymology* 420: 287-302), typically around 100-1000 times more than bone marrow. Also, fat is readily accessible, is present in all individuals and it is readily regenerated by the body. Additionally or alternatively, autologous bowel cells may be used, optionally in combination with autologous mesenchymal stem cells. The bowel cells may a comprise mixture of cells, such as epithelial cells, mesenchyme and intestinal stem cells, either separately or aggregated into multicellular organoid units. A small proportion of intestinal cells, such as organoid-type units, may act as a seed or template to help drive appropriate differentiation of co-seeded adipose-derived cells and naturally infiltrating cells after implantation.

Preferably, autologous cell isolation and reseeding of the decellularised scaffold is performed in the operating theatre, with minimal cell manipulation. The reseeded scaffold may then be anastomosed to a blood supply in the patient to ensure perfusion of the scaffold and delivery of oxygen, nutrients and cells to the scaffold. The reseeded, perfused scaffold may then be placed in the abdomen of the patient, preferably with a stoma as the distal end and connected to the existing bowel of the patient, but off-circuit from existing bowel flow. The patient then effectively takes the role of a bioreactor and bowel regeneration may occur by natural tissue regeneration. The stoma may be used as a visualisation means to determine the progress of bowel regeneration in the reseeded scaffold. Once sufficient regeneration has taken place, the now functional bowel may be anastomosed in the patient's existing bowel and connected in-circuit with bowel flow.

In alternative embodiments, reseeding of the decellularised scaffold may be performed outside the operating theatre, for example in a laboratory or in a bioreactor, to provide a regenerated 'organ' with some function that can then be 'transplanted' to the patient.

Stem cells are pluripotent, that is, they can give rise to many different cell types specific to particular tissues or organs. The decellularised intestinal scaffold contains the natural tissue structure, recognisable to cells as the native, natural structure of the intestine. This structural or topographical 'message' will signal the stem cells to differentiate into cells specific to that organ by a process of matrix-guided regeneration. The cells then multiply to repopulate the scaffold and develop biochemical/physiological functions specific to the bowel, thus creating a functional, living organ from the patient's own cells.

Thus, methods of the present invention may include a step of reseeding the implant with cells. Similarly, the implants of the present invention may be reseeded implants reseeded with cells.

According to a further aspect of the present invention there is provided an implant as herein described, the implant being reseeded with cells.

According to a further aspect of the present invention there is provided an apparatus for the processing of intestinal tissue according to a method as herein described, the intestinal tissue comprising a tubular segment of intestine with at least part of its associated vasculature intact, the apparatus comprising:
  a first perfusion circuit for perfusing the vasculature through a vessel thereof with at least one decellularising medium; and
  a second perfusion circuit for separately perfusing the tubular segment of intestine through its lumen with at least one decellularising medium.

The perfusion circuits may comprise tubes, hoses, pipes or the like, arranged to deliver the respective decellularising media for perfusion of the vasculature and the tubular intestinal component.

One or more pumps may be provided to ensure effective perfusion.

An incubation container may be provided for containment of an incubation medium, as herein described.

A further aspect of the present invention comprises the use of an apparatus as herein described in the manufacture of an implant.

According to a further aspect of the present invention there is provided an implant produced using a process and/or apparatus as herein described.

According to a further aspect of the present invention there is provided a method of treatment comprising the step of surgically implanting into a patient an implant as herein described.

According to a further aspect of the present invention there is provided the use in surgery of an implant as herein described.

According to a further aspect of the present invention there is provided an implant as herein described for use in surgery.

According to a further aspect of the present invention there is provided the use of an implant as herein described in the manufacture of a product for use in surgery.

DETAILED DESCRIPTION OF THE DRAWINGS

Embodiments of the present invention will now be further described with reference to the following non-limiting examples and accompanying figures in which.

DETAILED DESCRIPTION

Figure 1:
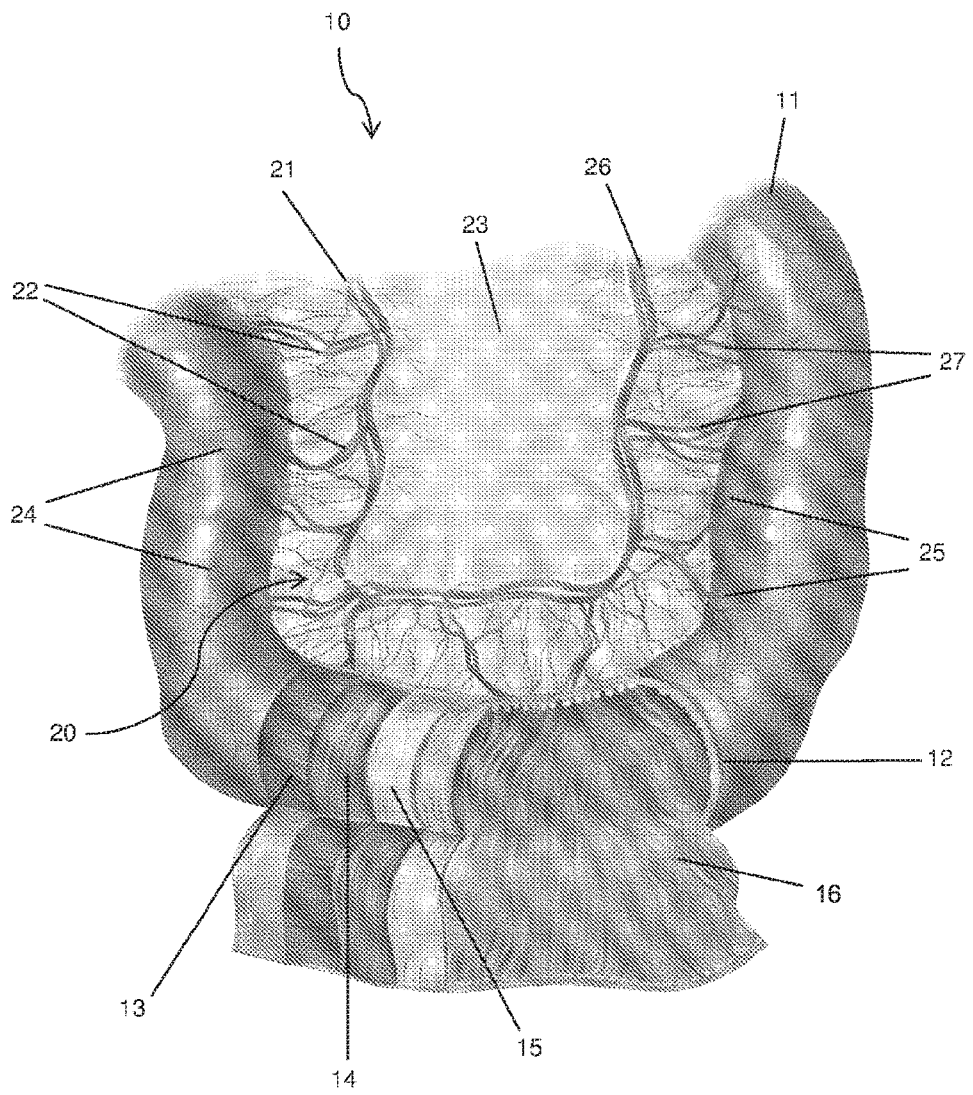
FIG. 1 is a diagrammatic representation of the anatomy of the small intestine and its associated vasculature.

The small intestine and its associated vascular structures (10) are depicted in FIG. 1. The small intestine is a tubular structure (11) with a central lumen. The tubular structure is comprised of an outer serosal layer (12) covering two muscle layers comprising a longitudinal (13) and a circular (14) muscle layer. Under the muscle layers is the bowel submucosa (15) which is covered (in the internal aspect of the bowel lumen) by a mucosal layer (16) whose microstructure is comprised of villi, microvilli and crypts. The small intestine also has a blood supply comprising feeding (arterial) and draining (venous) vessels forming a vascular tree (20) ultimately becoming integral and associated with the small intestine tissue in the form of feeding arterioles and capillaries (arterial supply side) and draining capillaries and venules (venous return side).

On the arterial (feeding) side, a feeding artery (21) has multiple sub-arterial branches (22) feeding various parts of the small intestine. The arteries and branches thereof are located in the vascular pedicle and surrounded and supported by connective tissue (the mesentery) (23). The arterial branches feed the small intestine associated/integral arterioles and capillaries (24). These vessels are located on and within the small intestine tissue and serve to perfuse the small intestine tissue with blood and other fluids and cells. Blood and fluids drain from the small intestine via integral venous capillaries and venules (25) which are located on and within the small intestine tissue. These vessels subsequently drain or return blood and fluids to the main venous return (vein) (26) via multiple venous branches (vein branches from the main draining vein) (27).

EXAMPLES

All reagents were purchased from Sigma-Aldrich (UK) or Fisher Scientific (UK).

All animals were maintained and handled in accordance with the Animals Scientific Procedures Act 1986 and studies were performed following guidelines stipulated and licensed by the UK Home Office. Experiments were performed using Large White Landrace crossbreed pigs. All animals were kepy under standard laboratory conditions and fed a commercial pelleted diet.

Figure 3:
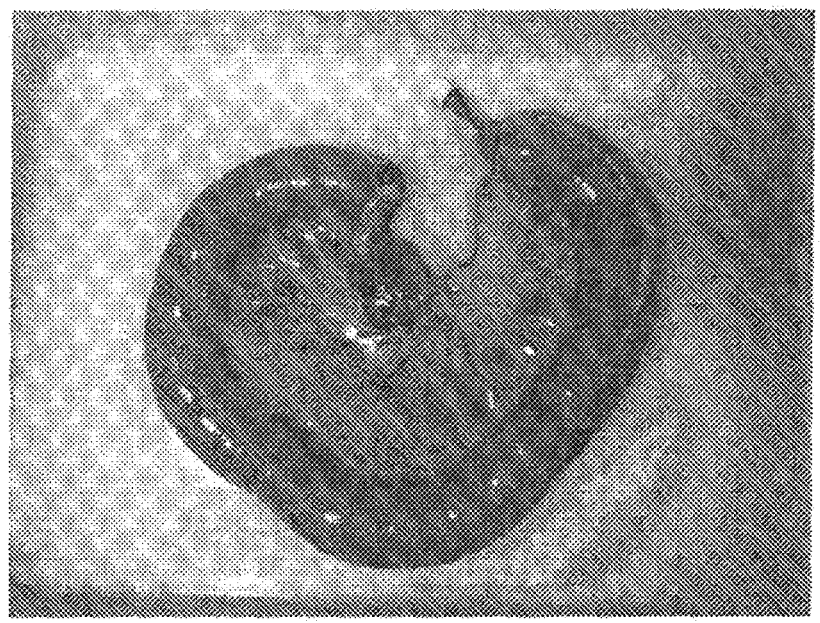
FIG. 3 is a photograph showing a tubular segement of intestinal tissue with intact vasculature before treatment.

1. Preparation of Acellular Scaffold (a) Harvesting of Porcine Intestinal Tissue Following intravenous administration of heparin (7,000 U) in a 60-65 kg Large White Landrace crossbreed pig, a midline incision was created and segment of ileum was isolated together with its attached vascular supply approximately 20-30 cm in length. Residual lymph nodes in the mesentery were dissected; keeping the whole specimen leak proof; the distal end of the pedicle was tied off and isolated. The proximal end of the artery was cannulated with a 14 G Radiopaque I.V. cannula and flushed with 0.9% NaCl containing heparin (2,000 U) until there was no blood in the outflow at the proximal end of the vein. To maintain intraluminal pressure within the vasculature and maintain patency, a pulsatile pump perfusing heparinised (2000 U/I) 0.9% NaCl through the pedicle was attached to the arterial cannula. All vessels not involved in supplying the small intestine that was to be explanted were tied off, and the whole explant was removed from the animal. At the end of the procedure, the animal was terminated by intravenous overdose of anaesthesia. The vascular circuit was checked for any leakage and the intestinal lumen was flushed with 1 liter of 0.9% NaCl. At both ends of the ileal segment, silicone tubes were attached with purse-string sutures, and the segment of small intestine was attached to the second perfusion circuit. The harvested specimen was then ready for decellularisation. FIG. 3 shows a representative specimen prepared as described above. The bowel segment has been filled with saline and clamped at either end, aiding visualisation of the bowel structure, vascular system and fine capillaries overlying the serosal surface. The mesenteric arcade, in which the feeder arterial vessels and return venous vessels can clearly be seen, forms a fan-like structure in the inner portion of the bowel segment loop. The bowel segment has a pink appearance due to presence of cells and blood in the vessels and tissues.

(b) Decellularisation of the Porcine Intestinal Tissue

Immediately after explantation, two separate perfusion circuits were set up for decellularisation of the vascular component and the tubular intestinal component.

Figure 2:
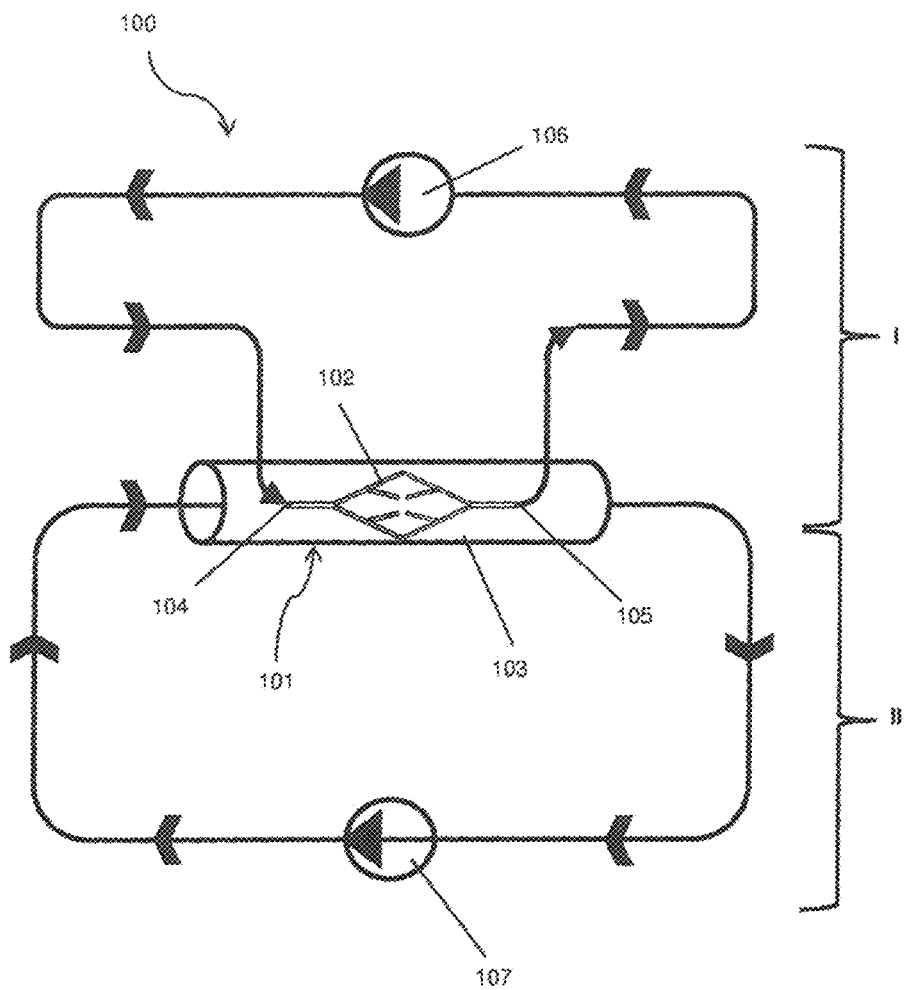
FIG. 2 is a schematic diagram of a perfusion system according to the present invention.

As shown in schematic form in FIG. 2, a perfusion system (100) was set up for processing the intestinal tissue (101) comprising a vascular component (102) and a tubular intestinal component (103). Circuit I was attached via a cannula into the main artery (104) of the mesenteric arcade and exited via the main vein (105) and circuit II was attached to the silicone tubes tied to each end of the explanted tubular segment of ileum (103). Pumps (106, 107 respectively) were used to pump decellularising media separately around circuits I and II, the arrows representing the direction of flow.

The decellularisation protocol used is presented in Table 1:

TABLE 1

CIRCUIT I AND II

| | Solution | Time | Temperature |
|---|---|---|---|
| 1. | 0.075% SDS solution | 90 min | 25° C. |
| 2. | Antibiotics solution | 3 changes; 15 min each | 25° C. |
| 3. | 0.05% Trypsin solution | 90 min | 37° C. |
| 4. | Antibiotics solution | 3 changes; 15 min each | 25° C. |
| 5. | DNase I solution | 120 min | 37° C. |
| 6. | Antibiotics solution | Overnight | 4° C. |
| 7. | 0.075% SDS solution | 90 min | 25° C. |
| 8. | Antibiotics solution | 3 changes; 15 min each | 25° C. |
| 9. | 0.05% Trypsin solution | 90 min | 37° C. |
| 10. | Antibiotics solution | 3 changes; 15 min each | 25° C. |
| | Circuit I | | |
| 11. | Antibiotics solution | Till the end of process | 25-37° C. |
| | Circuit II | | |
| 11. | 0.075% SDS solution | 90 min | 25° C. |
| 12. | Antibiotics solution | 3 changes; 15 min each | 25° C. |
| 13. | 0.05% Trypsin solution | 90 min | 37° C. |
| 14. | Antibiotics solution | 3 changes; 15 min each | 25° C. |

The intestinal tissue was submerged in the solutions used for perfusion through circuit I. Perfusion was conducted using a Watson Marlow 323S/D Pump (UK) at the rate of 30-60 rpm throughout the whole process. The cells, cytoplasmic components and finally deoxyribonucleic acids were broken down by serial perfusions of SDS, trypsin and DNase I solutions washed in between each step with PBS supplied with antibiotics. After the last stage of the decellularisation, the cannula was detached from the artery and the silicone tubes from the ileum. The acellular scaffold was sterilized by placing it in a solution of 0.1% peracetic acid in PBS on a horizontal shaker for three hours at room temperature. Subsequently, the specimen was washed in sterile PBS supplemented with antibiotics, and stored in sterile PBS supplied with antibiotics till further use.

Figure 4:
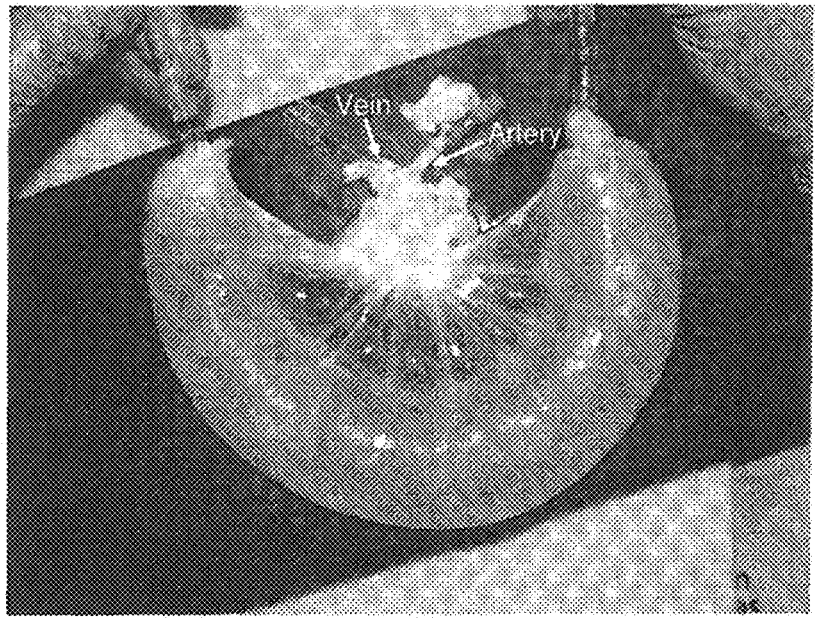
FIG. 4 is photograph showing a representative implant according to the present invention, produced from the starting material shown in FIG. 3.

The resulting decellularised implant is shown in FIG. 4. The decellularised bowel implant has an off-white, semi-translucent appearance following removal of cells and blood. The tubular bowel component is shown clamped and filled with saline solution, allowing better observation of the preserved bowel structure, mesenteric arcade and the fine capillaries overlying the serosal surface. The mesenteric arcade forms a fan-like structure in the inner portion of the bowel segment loop. The feeding arterial vessel and venous return vessel are cannulated and clearly visible.

(c) Histological and Molecular Analysis of Acellular Scaffold

Three representative acellular scaffolds were subjected to histological and molecular analysis for the presence of nuclear material. Intestinal tissue from animals of the same age and weight were used for comparative purpose; samples from the entire length of the de-cellularised ileal and mesenteric arcade scaffold were fixed in 10% NBF and processed for wax embedding using routine laboratory procedures. Sections were cut at 5 µm and stained with Haematoxylin and Eosin (H&E) and Picro-Sirius red with Miller's elastin (PSR-ME).

0.025 g from each scaffold was used for DNA isolation using GenElute Mammalian Genomic DNA Miniprep Kit (Sigma-Aldrich, UK) according to the manufacturer's instructions. The amount of DNA residual in the vascular and intestinal part of the scaffold-construct as well as DNA isolated from native ileum and associated vessels were quantified using spectrophotometer (AD=260). Electrophoretic separation of DNA was conducted in order to visualise the differences in the presence of DNA in the samples of acellular scaffold and native tissues. DNA was separated on 1% agarose gel in Tris-acetate Ethylendiaminetetraacetic Acid (TAE) buffer for 2 h at 100V. Subsequently, the gel was stained with ethidium bromide solution for 15 min.

The quantity of GAGs in the acellular scaffolds was assessed using Blyscan Sulphated Glycosaminoglycan Assay (Biocolor; UK) according to the manufacturer's instructions. The assay was used to calculate the total sulphated glycans content according to spectrophotometric (650 nm) absorbance values of sulphation level (dye-binding capability) as calculated using the supplied assay standards (range 2-50 µg/ml) of GAGs. The GAGs were isolated from three different batches of specimen, and the concentration was calculated using standard curve. The results are presented as µg/g of wet weight. Values obtained for the acellular scaffold were compared to values for control porcine intestinal tissue.

Figure 5:
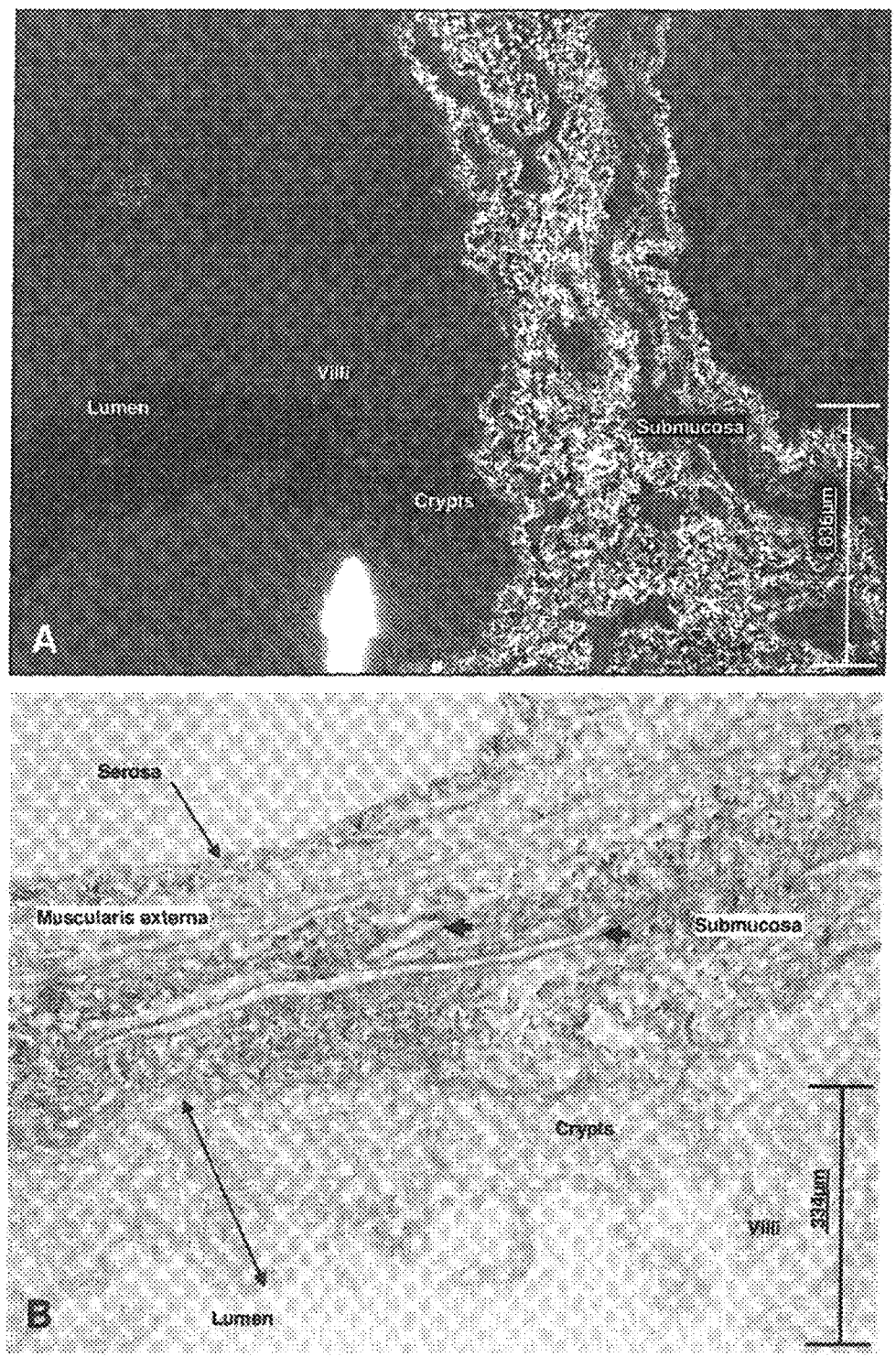
FIG. 5A is a photomicrograph (×40 final magnification) showing a section of a representative implant according to the present invention, stained with Picro Sirius Red and viewed under polarised light.
FIG. 5B is a photomicrograph (×100 final magnification) showing a section of a representative implant according to the present invention, stained with Picro-sirius red and Miller's elastin. The double arrow shows the mucosal layer and the small arrows point to preserved elastin within small-calibre submucosal vessels.

Histological analysis of the decellularised scaffold showed no intact cells in either the vascular mesenteric arcade or the ileal tissue. Analysis of the tissue under polarised light on PSR-ME stained sections showed good vascular preservation of collagen and elastin, with mainly yellow-to-orange collagen fibres of the submucosa and thin, green fibres of the mucosal layer appearing similar to native intestine (see FIG. 5A). Staining with H&E confirmed that elastin was preserved even within the small-calibre submucosal vessels (see FIG. 5B).

Although some residual DNA was detected in both the vascular and intestinal part of the decellularised scaffold, it represented a significant decrease when compared with native tissue. The total amount of DNA found within the tubular intestinal component of the decellularised scaffold constituted only 0.75% of total DNA found in native tissue, whereas the decellularised vasculature had less than 1% of the total DNA found in native blood vessels (Table 2). There was decrease in the amount of GAGs remaining after the de-cellularisation process; overall there was a 42% retention of functional GAGs within the decellularised scaffold (Table 2).

TABLE 2

| Specimen | DNA (standard deviation) [ug/mg] | GAG's (standard deviation) [ug/g] |
|---|---|---|
| Native ileal tubular component | 0.74 (0.17) | 3.1 (0.05) |
| Native vascular component | 0.36 (0.08) | 2.9 (0.03) |
| Decellularised ileal tubular component | 0.005 (0.002) | 0.005 (0.005) |
| Decellularised vascular component | 0.004 (0.002) | 0.9 (0.03) |

3. Implantation of the Acellular Scaffold into Porcine Recipient (a) Surgical Procedure Large White Landrace crossbreed pigs (n=7), (55-75 kg) underwent a right-sided nephrectomy via a midline incision. The vascular component (feeding artery and draining vein of ileal pedicle) of the scaffold was anastomosed in an end-to-end fashion to the renal artery and vein. The anastomotic site as well as the mesenteric vasculature of the implanted scaffold construct was checked for any bleeding. Mersilk ties were used to stem excess blood loss. Once blood was observed perfusing through the mesenteric arcade and the fine capillary network encasing the decellularised ileum, the entire scaffold implant was placed into the kidney cavity for one hour and the animal's physiological signs monitored. Thereafter, the animal was terminated with a lethal injection of sodium pentobarbitone (100 mg/kg).

One scaffold was implanted for a recovery procedure for 24 hours. The scaffold was placed into the kidney cavity and the abdominal muscle layers were closed using intramuscular suture (3.0 Vicryl) and skin using horizontal mattress suture (3.0 Mersilk). Post-operatively, the animal received analgesia using intravenous Carprofen (4 mg/kg body weight). After 24 hours the animal was terminated and the graft immediately harvested.

Prior to surgical implantation of the scaffold, an anti-coagulation protocol was applied. This comprised pre-treatment of the animal with anti-thrombotic drugs prior and during the surgical procedure as well as pre-conditioning the vascular part of the implant by injecting it with either neat or dissolved heparin sodium in saline solution, as shown in Table 3.

TABLE 3

| Animal no. | Procedure (terminal/ recovery) | Weight of pig [kg] | Heparin sodium administered systemically during implantation [U] | Heparin sodium applied into scaffold prior to implantation [U] | Total heparin sodium received by animal/kg/h of surgical procedure | Additional anti-coagulative/ platelet-formation drugs received by animal [U/kg/h] |
|---|---|---|---|---|---|---|
| 1. | Terminal | 55 | 1. Post-incision: 7,000<br>2. Prior to releasing the vascular clamps: 1,000 | 1,000 | 55 | — |
| 2. | Terminal | 55 | 1. Post-incision: 7,000<br>2. Prior to releasing the vascular clamps: 2,000 | 1,000 | 51 | — |
| 3. | Terminal | 73 | 1. Post-incision: 7,000<br>2. Prior to releasing the vascular clamps: 2,000<br>3. Administered into graft's feeding artery: 2,000 | 1,000 | 82 | 1. Warfarin: 12 mg/day starting 3 days prior to surgery |
| 4. | Terminal | 70 | 1. Post-incision: 10,000<br>2. Prior to releasing the vascular clamps: 10,000 | 30,000 | 260 | 1. Warfarin: 12 mg/day starting 3 days prior to surgery |
| 5. | Terminal | 70 | 1. Post-incision: 10,000<br>2. Prior to releasing the vascular clamps: 10,000 | 30,000 | 260 | 1. Warfarin: 12 mg/day starting 3 days prior to surgery |
| 6. | Terminal | 75 | 1. Post-incision: 10,000<br>2. Prior to releasing the vascular clamps: 10,000 | 35,000 | 298 | 1. Warfarin: 12 mg/day starting 2 days prior to surgery<br>2. Clexane: 120 mg on the day of surgery |
| 7. | Recovery (24 hours) | 55 | 1. Post-incision: 10,000<br>2. Prior to releasing the vascular clamps: 2,000 | 30,000 | 255 | 1. Warfarin: 12 mg/day starting 3 days prior to surgery |

Figure 6:
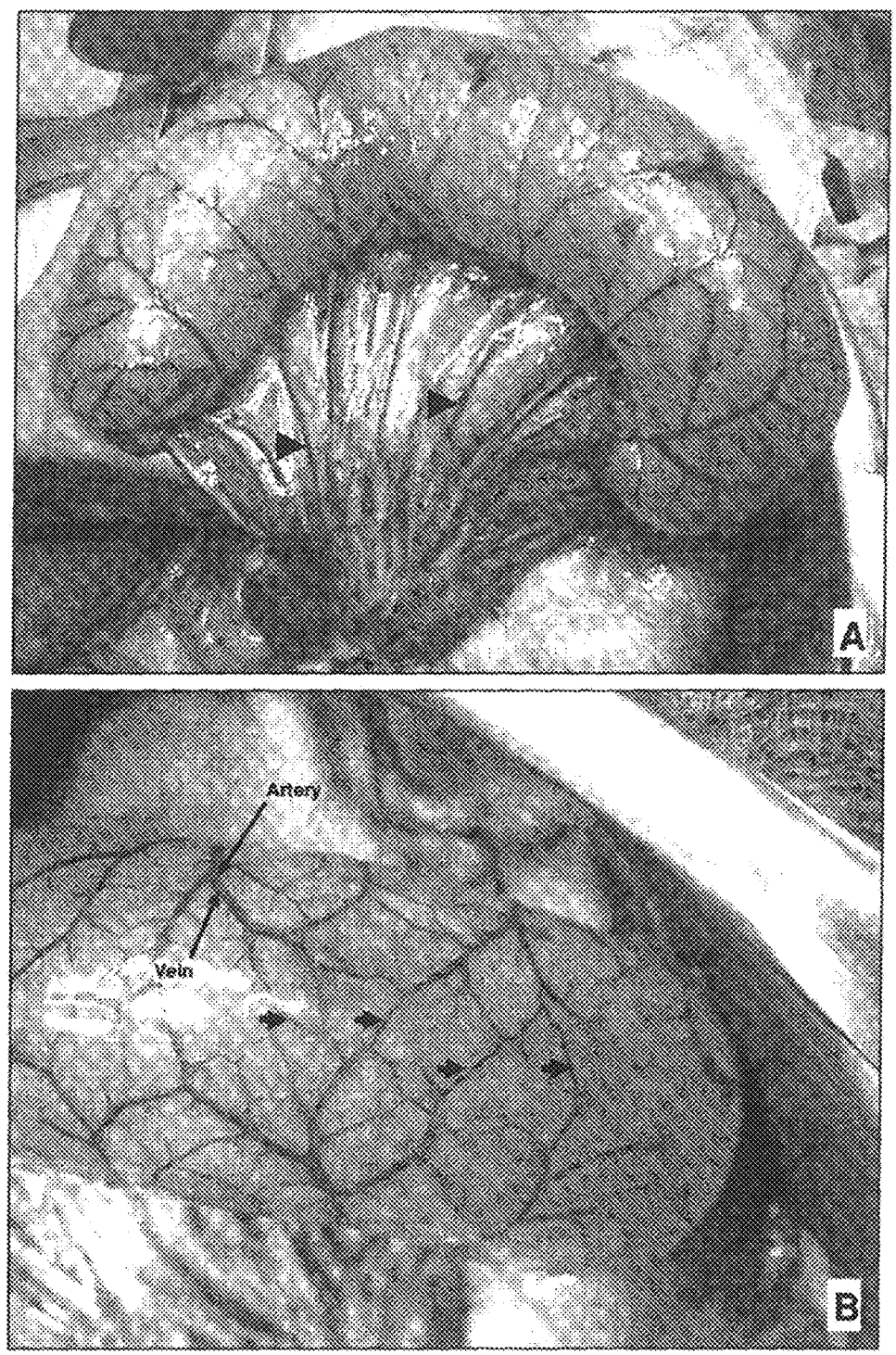
FIG. 6A is a photograph showing a representative implant according to the present invention 1 hour post-implantation into a porcine recipient. The arrow heads point to clot-free mesenteric vessels.
FIG. 6B is a photograph showing an alternative view of the implant of FIG. 6A. The arrows point to intestinal micro-connections with distinguishable decellularised vessels.

Successful end-to-end anastomosis of the de-cellularised artery and vein to the renal artery and vein of the recipient animal was achieved in all animals. In five out of seven implants, complete reperfusion of the scaffold (including vascular micro-connections within the decellularised bowel with the host's blood) was obtained within one hour of implantation (see FIG. 6), and the scaffolds remained patent for the duration of the experiment (Table 5). The seventh graft left in vivo for 24 hours was patent at the time of explantation.

FIG. 6A shows the implant 1 hour post-implantation. The perfused bowel-derived segment has a healthy pink appearance typical of vital, perfused tissues. The mesenteric arcade shows good perfusion, as does the bowel implant. The arrow heads point to clot-free mesenteric vessels and complete perfusion of the microvessels on the serosal surface of the bowel segment is visible.

FIG. 6B provides an alternative view of the same implant 1 hour post-implantation, at a higher magnification than that depicted in FIG. 6A. The arrows point to bowel microconnections with distinguishable decellularised vessels. The image shows clot free and patent vascular system with arteries and veins clearly visible and perfused with the recipient's blood. The capillaries on the serosal surface are also clearly visible, perfused and structurally intact following decellularisation as evidenced by no leakage of blood. The perfused bowel segment has a healthy pink appearance typical of vital, perfused tissues.

Successful reperfusion of the grafts with systemic blood was obtained in five out of the seven cases. In the two unsuccessful cases, reperfusion was prevented by clotting of the mesenteric vessels, which took place shortly after introducing the systemic blood to the scaffold. The most successful protocol combined oral pre-medication of the animals with 12 mg/day of Warfarin, pre-conditioning of the scaffold construct with 30.000 U of neat sodium heparin and intravenous infusion of 12,000-20,000 U of sodium heparin. Animals with a total heparin intake (calculated based on body weight and the length of the surgical procedure) of 255-260 U/kg/h were anticoagulated best. However, animals receiving 55 U/kg/h also had a satisfactory outcome with complete reperfusion and patency of the decellularised vessels, as shown in Table 4:

TABLE 4

Outcome of the implantation

| Animal no. | Successful anastomosis | Re-perfusion with blood | Clot formation | Excessive bleeding |
|---|---|---|---|---|
| 1. | + | + | − | − |
| 2. | + | − | + | − |
| 3. | + | − | + | − |
| 4. | + | + | − | − |
| 5. | + | + | − | − |
| 6. | + | + | − | +++ |
| 7. | + | + | − | + |

The length of the decellularised feeding artery and draining vein also contributed to whether reperfusion was likely or not, since scaffolds with shorter vessels performed better (see Table 5).

TABLE 5

| Animal no. | Length of the pedicle [cm] Artery | Length of the pedicle [cm] Vein | Average length of implanted vessels | Total heparin recieved by animal regarding length of implanted vessels [U/kg/h/cm] |
|---|---|---|---|---|
| 1. | 1 | 0.5 | 0.75 | 73 |
| 2. | 3.0 | 2.5 | 2.75 | 30 |
| 3. | 3.5 | 2.5 | 3 | 17 |
| 4. | 3 | 2.35 | 2.675 | 30 |
| 5. | 2 | 1.95 | 1.975 | 131 |
| 6. | 1.9 | 1.9 | 1.9 | 137 |
| 7. | 1.95 | 1.95 | 1.95 | 153 |
| 8. | 2 | 1.85 | 1.925 | 132 |

(b) Histological and Immunohistochemical Analysis

Following each implantation procedure, samples from the scaffold were removed, fixed and processed for routine histology. H&E stained sections were used to assess the degree of vascular leakage into the surrounding tissue, rate of perfusion and any signs of clotting within the blood vessels.

Immuno-histochemical staining was incorporated in order to visualize any endothelial progenitor cells (CD133), smooth muscle actin (αSMA), macrophages (CD68) and Von Willebrand Factor (vWF) within the grafts harvested 1 and 24 hours post-implantation. Prior to IHC staining all sections were de-waxed and rehydrated and any necessary antigen retrieval was carried out at this point. Endogenous peroxidise activity within the tissue was blocked using 3% hydrogen peroxidise in methanol for 30 minutes. Non-specific binding was prevented using normal horse serum (Impress Kit, Vector Laboratories, UK) for 30 minutes (CD68 αSMA) and 2 hours (CD133, VWF). Sections where then incubated with the primary antibody diluted in PBS; for negative controls performed in parallel, only PBS was used. Sections were subsequently washed in PBS; 3×3 minute washes cycles and then incubated further with a biotinylated secondary antibody. This step was followed by Vectastain Elite ABC kit (Vector Laboratories, UK) and 3×3-minute cycles with PBS (CD133). Visualization was achieved using 3,3-diaminobenzidine tetrachloride (DAB) substrate (Vector Laboratories. UK), and 5 minutes wash in distilled water. Finally, sections were counterstained with Harris haematoxylin for 1 minute, dehydrated, cleared in xylene and cover slipped.

All continuous data was expressed as the mean (n=3) ±Standard Error of the Mean (SEM) and $p<0.05$ was taken as significant. p Values were estimated using one-way ANOVA, and all computations were performed using GraphPad Prism 4 software.

Figure 7:
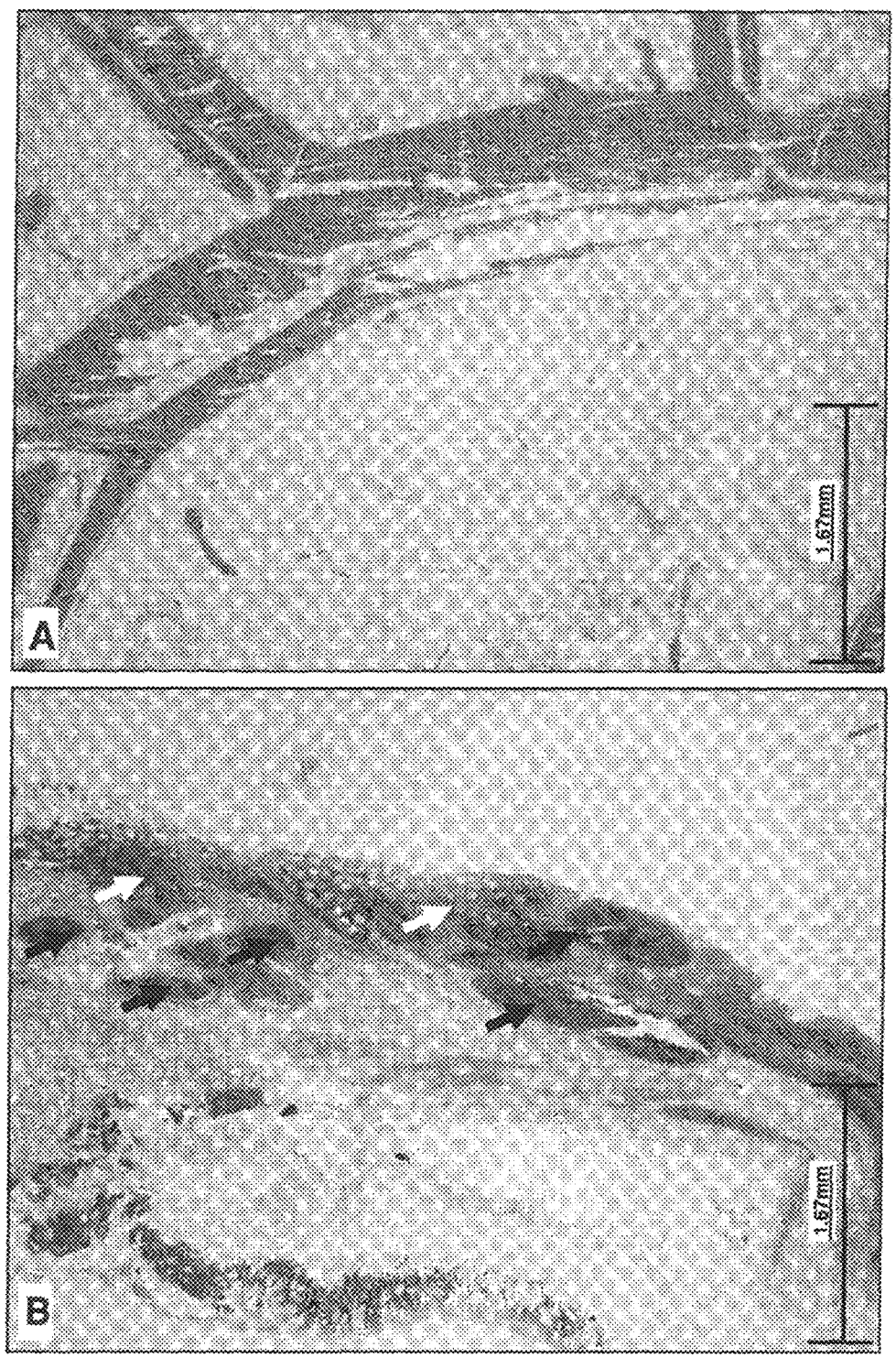
FIG. 7A is a photomicrograph (×20 final magnification) showing a section of a representative implant according to the present invention, stained with haematoxylin and eosin 1 hour post-implantation into a porcine recipient. This longitudinal section shows mesenteric vein and artery with clot-free lumens.
FIG. 7B is a photomicrograph (×20 final magnification) showing a section of a representative implant according to the present invention, stained with haematoxylin and eosin 24 hours post-implantation into a porcine recipient. This cross section of the mesenteric arcade shows clot-free vessels (dark arrows) and inflammatory cells infiltrating the outer parts of the graft (light arrows).

Histological analysis indicated that in five out of the seven implants (four short and one long-term study) the majority of vessels (including intestinal small diameter vessels and capillaries) were patent and contained non-coagulated blood (see FIG. 7A, B). Miller's elastin staining indicated that clotting was mostly triggered in places where the vascular wall or internal elastin was interrupted.

Figure 8:
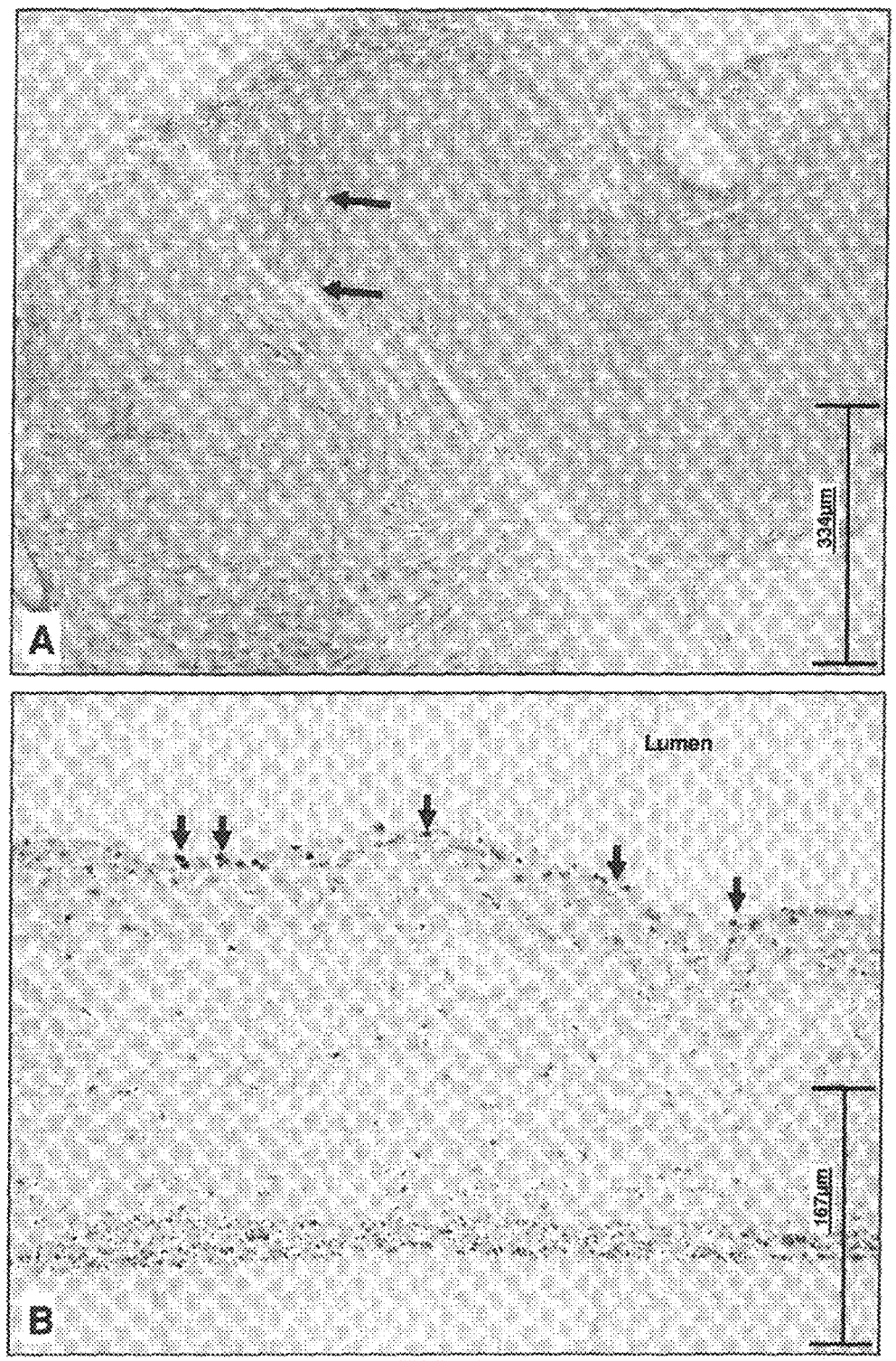
FIG. 8A is a photomicrograph (×100 final magnification) showing a section of a representative implant according to the present invention, stained with haematoxylin and eosin 1 hour post-implantation into a porcine recipient. This longitudinal section of the arterial anastomotie site of the graft shows host cells infiltrating the decellularised superior mesenteric artery (see arrows).
FIG. 8B is a photomicrograph (×200 final magnification) showing a section of a representative implant according to the present invention, stained with haematoxylin and eosin 24 hours post-implantation into a porcine recipient. The arrows point to CD133+ cells lining lumen of the decellularised artery of the graft.

As early as one hour post-implantation host cells were present in the anastomosed, acellular vessels of the scaffolds (FIG. 8A). The rate of cellular infiltration was reduced in the distal parts of the graft. Nevertheless, cells were present on the luminal surface of the mesenteric vessels. The rate of cellular infiltration of the scaffold ECM was very high 24 hours post-implantation, but no signs of intensive foreign body reaction could be characterised.

The majority of cells infiltrating from the anastomotic side of the arteries at one hour were CD68+, however, 24 hours later more macrophages were present in the distal than in the proximal parts of the implanted vessels. Most of the cells present in the main artery (but not the vein) of the graft implanted for 24 hours were CD68−. There were more macrophages within the clot-free parts of the scaffold-constructs. Few CD68+ cells were present in the host's renal vessels. Some of the cells lining the anastomosed artery were CD133+ as early as one hour post-implantaton, and their number increased within 24 hours (see FIG. 8B). Sections of anastomotic site showed similar amount of VWF+ staining in the donor and recipient main pedicle. However, no staining was detected when un-implanted decellularised main artery and vein were analyzed. No αSMA+ cells could be seen in any of the implants.

It is of course to be understood that the invention is not intended to be restricted by the details of the above specific embodiments, which are provided by way of example only.

The invention claimed is:

1. A method for producing an implant from intestinal tissue comprising a tubular segment of intestine with at least part of its associated vasculature intact, the method comprising:

perfusing the vasculature through a vessel thereof with a first perfusion protocol, wherein the first perfusion protocol comprises perfusing the vasculature with a first series of decellularizing media for a first perfusion time period, wherein the first series of decellularizing media includes at least three decellularizing media comprising a first media including at least one detergent, a second media including at least one protease, and a third media including at least one DNase, and wherein the vasculature is washed in between each decellularizing medium with a first washing medium;

separately perfusing the tubular segment of intestine through its lumen with a second perfusion protocol, wherein the second perfusion protocol comprises perfusing the tubular segment with a second series of decellularizing media for a second perfusion time period, wherein the second series comprises at least one detergent, at least one protease and at least one DNase, and wherein the tubular segment is washed in between each decellularizing medium with a second washing medium that is the same or different than the first washing medium;

washing the implant after the second perfusion protocol with the first washing medium and/or the second washing medium;

wherein perfusion of the vasculature is carried out according to a first perfusion protocol and perfusion of the tubular segment of intestine is carried out according to a second, different protocol;

wherein the first and second perfusion protocols differ in at least one of: a) the detergent, b) the protease, c) the DNase, d) the second perfusion protocol comprises a greater number of perfusion steps comprising detergent, protease or DNase, than the first perfusion protocol, e) the second perfusion protocol is performed for a longer period than the first perfusion protocol, or f) combinations thereof.

2. A method according to claim 1, wherein the vasculature is perfused through a main artery thereof and wherein the at least one decellularising medium of the series of media perfusing the vasculature leaves the vasculature via a main vein.

3. A method according to claim 1, wherein cells are substantially removed from the intestinal tissue.

4. A method according to claim 1, wherein perfusion of the vasculature, perfusion of the tubular segment, or both, is carried out using serial perfusions of solutions of sodium dodecyl sulfate (SDS), trypsin and DNase.

5. A method according to claim 1, wherein any one or more of the following structures are at least partially retained in the implant: mucosal layer of the tubular component, submucosal layer of the tubular component, serosal layer of the tubular component, circular and/or longitudinal muscular layers of the tubular component, tunica adventitia of the vasculature, tunica media of the vasculature, or tunica intima of the vasculature.

6. A method according to claim 1, wherein the implant comprises an internal elastic lamella and an elastin layer of the internal elastic lamella is substantially preserved and forms an internal, luminal, surface in the vascular portion of the implant.

7. A method according to claim 1, wherein an input means and/or an output means are attached to a proximal end and/or a distal end of the tubular segment of intestine to facilitate perfusion of the tubular segment of intestine.

8. A method according to claim 1, wherein the washing media are free of any decellularizing agents.

* * * * *